US010538442B2

(12) United States Patent
Kramer

(10) Patent No.: US 10,538,442 B2
(45) Date of Patent: Jan. 21, 2020

(54) WATER TREATMENT

(71) Applicant: BWA WATER ADDITIVES UK LIMITED, Manchester (GB)

(72) Inventor: Jeffrey Frank Kramer, Tucker, GA (US)

(73) Assignee: BWA WATER ADDITIVES UK LIMITED, Greater Manchester (GB)

( * ) Notice: Subject to any disclaimer, the term of this patent is extended or adjusted under 35 U.S.C. 154(b) by 0 days.

(21) Appl. No.: 14/840,674

(22) Filed: Aug. 31, 2015

(65) Prior Publication Data
US 2017/0057851 A1    Mar. 2, 2017

(51) Int. Cl.
| C02F 1/76 | (2006.01) |
| A01N 57/34 | (2006.01) |
| A01N 59/00 | (2006.01) |
| A01N 57/20 | (2006.01) |
| A01N 35/04 | (2006.01) |
| C02F 103/02 | (2006.01) |
| C02F 103/28 | (2006.01) |
| C02F 103/36 | (2006.01) |

(52) U.S. Cl.
CPC ............. *C02F 1/76* (2013.01); *A01N 35/04* (2013.01); *A01N 57/20* (2013.01); *A01N 57/34* (2013.01); *A01N 59/00* (2013.01); *C02F 2103/023* (2013.01); *C02F 2103/28* (2013.01); *C02F 2103/365* (2013.01)

(58) Field of Classification Search
CPC .... C02F 1/76; C02F 2303/04; C02F 2103/23; C02F 2103/28; C02F 2103/365; A01N 59/00; A01N 57/34
USPC .................................................. 424/486, 405
See application file for complete search history.

(56) References Cited

U.S. PATENT DOCUMENTS

| 3,281,365 | A | | 10/1966 | Moedritzer |
| 4,835,143 | A | | 5/1989 | Donofrio et al. |
| 4,874,526 | A | * | 10/1989 | Grade ....................... C02F 1/50 |
| | | | | 210/697 |
| 5,063,213 | A | | 11/1991 | Whitekettle et al. |
| 5,063,214 | A | * | 11/1991 | Whitekettle ........... A01N 57/34 |
| | | | | 162/161 |
| 5,063,218 | A | | 11/1991 | Whitekettle et al. |
| 5,102,874 | A | | 4/1992 | Lintner et al. |
| 5,376,731 | A | | 12/1994 | Kerr et al. |
| 5,741,757 | A | | 4/1998 | Cooper et al. |
| 6,241,898 | B1 | | 6/2001 | Wright et al. |
| 6,419,879 | B1 | | 7/2002 | Cooper et al. |
| 6,471,974 | B1 | | 10/2002 | Rees et al. |
| 6,478,972 | B1 | | 11/2002 | Shim et al. |
| 6,669,904 | B1 | | 12/2003 | Yang et al. |
| 2005/0061753 | A1 | | 3/2005 | Dickinson |
| 2006/0006121 | A1 | | 1/2006 | Simpson et al. |
| 2006/0032823 | A1 | | 2/2006 | Harrison et al. |
| 2006/0113251 | A1 | | 6/2006 | McGuire et al. |
| 2007/0012632 | A1 | | 1/2007 | Simons |
| 2009/0050320 | A1 | | 2/2009 | Collins et al. |
| 2009/0229827 | A1 | | 9/2009 | Bryant et al. |
| 2010/0200239 | A1 | | 8/2010 | Aften |
| 2010/0226874 | A1 | | 9/2010 | Kramer et al. |
| 2011/0257788 | A1 | | 10/2011 | Wiemers et al. |
| 2012/0024794 | A1 | | 2/2012 | Fischmann |
| 2012/0087993 | A1 | * | 4/2012 | Martin ................... A01N 35/04 |
| | | | | 424/661 |
| 2012/0178722 | A1 | | 7/2012 | Yin |
| 2012/0223022 | A1 | * | 9/2012 | Hassler .................. C02F 1/281 |
| | | | | 210/717 |
| 2012/0285693 | A1 | | 11/2012 | Mirakyan et al. |
| 2014/0030306 | A1 | * | 1/2014 | Polizzotti ............... A01N 63/00 |
| | | | | 424/420 |
| 2014/0166588 | A1 | | 6/2014 | Fischmann |
| 2014/0194335 | A1 | | 7/2014 | Gu et al. |
| 2014/0301984 | A1 | * | 10/2014 | Corrin .................... A61K 35/76 |
| | | | | 424/93.6 |
| 2015/0056648 | A1 | | 2/2015 | Tidwell et al. |
| 2015/0225235 | A1 | | 8/2015 | Mcilwaine et al. |

FOREIGN PATENT DOCUMENTS

| EP | 0479465 A2 | 4/1992 |
| EP | 0681995 A1 | 10/1994 |
| GB | 2354771 A | 4/2001 |
| JP | 10273408 A | 10/1998 |
| JP | 2010167320 | 5/2010 |
| WO | 9104668 A1 | 4/1991 |
| WO | 0142145 A1 | 6/2001 |
| WO | 03031347 A1 | 4/2003 |

(Continued)

OTHER PUBLICATIONS

Haller et al, title: Determination of chlorine dioxide and other active chlorine compounds in water, Analytical chemistry, vol. 20; No. 7, Jul. 1948, pp. 639-642.*
Whole Health Organization (WHO), title: Total dissolved solids in drinking water, 2nd edition, vol. 2; 1996.*
Zehr; Front Microbiol.; 2010; 1:4, published online Jul. 20, 2010.*
Unknown author, title: definition of TDS, downloaded from https:// www.purewaterproducts.com/water-problems/total-dissolved-solids-tds Nov. 7, 2018. (Year: 2018).*

(Continued)

*Primary Examiner* — Yanzhi Zhang

(74) *Attorney, Agent, or Firm* — McNees Wallace & Nurick LLC

(57) ABSTRACT

The present invention relates to water treatment. In one embodiment there is provided a method of treating an aqueous system to inhibit growth of one or more microorganisms therein and/or to reduce the number of live micro-organisms therein. The method comprises adding treatment agents to said aqueous system and wherein said treatment agents comprise: (a) a phosphonium compound; and (b) a halogen oxide compound.

17 Claims, No Drawings

(56) References Cited

FOREIGN PATENT DOCUMENTS

| WO | 03073848 A1 | 12/2003 |
|---|---|---|
| WO | 2005123607 A1 | 12/2005 |
| WO | 2010100470 A2 | 9/2010 |

OTHER PUBLICATIONS

U.S. Appl. No. 14/513,693, filed Oct. 14, 2014, Kramer.
U.S. Appl. No. 14/513,735, filed Oct. 14, 2014, Kramer.
U.S. Appl. No. 14/513,768, filed Oct. 14, 2014, Kramer.
U.S. Appl. No. 14/673,419, filed Mar. 30, 2015, Kramer et al.
U.S. Appl. No. 14/870,951, filed Sep. 30, 2015, Kramer.
U.S. Appl. No. 14/872,399, filed Oct. 1, 2015, Kramer.
U.S. Appl. No. 14/874,686, filed Oct. 5, 2015, Kramer et al.
U.S. Appl. No. 14/878,240, filed Oct. 8, 2015, Kramer et al.
BWA Water Additives, "Product Label for Bellacide© 303," http://www.kellysolutions.com/erenewals/documentsubmit/KellyData%5COK%5Cpesticide%5CProduct%20Labe1%5C83451%5 C83451-20%5C83451-20 Bellacide 303 6 16 2011_2_54_43_PM.pdf.
BWA Water Additives, "Product Information for Bellacide© 303—Multi-purpose Non-oxidizing Biocide for Industrial Water Systems," http://www.wateradditives.com/Repository/Files/BWA_Bellacide_303_GP_WF_-_AsiaPac_O.pdf.
BWA Water Additives, "Technical Data for Bellacide© 303—Multi-purpose Non-oxidizing Biocide for Industrial Water Systems," http://www.wateradditives.com/Repository/Files/BWA_Bellacide_303_TI_WF_AsiaPac.pdf.
Kull, F C. et al., "Mixtures of Quaternary Ammonium Compounds and Long-chain Fatty Acids as Antifungal Agents," Applied Microbiology, Nov. 1961, pp. 538-541, vol. 9, No. 6, The American Society for Microbiology by the Williams & Wilkins Company, Baltimore, MD.
May, Oscar W., "Polymeric Antimicrobial Agents," Disinfection, Sterilization, and Preservation, Chapter 18, Jan. 1, 1991, pp. 322-333, Philadelphia, Lea & Febiger, US.
Rembaum, A, "Biological Activity of Ionene Polymers," Applied Polymer Symposium, 1973, pp. 299-317, No. 22, J. Wiley & Sons, Inc., New York, NY.
U.S. Appl. No. 12/399,300, Final Office Action dated Feb. 23, 2016, 14 pages.
U.S. Appl. No. 14/513,693, Non-Final Office Action dated Feb. 26, 2016, 11 pages.
Giri, Jitendra et al., "Effluents from Paper and Pulp Industries and their impact on soil properties and chemical composition of plants in Uttarakhand, India," Journal of Environment and Waste Management, May 2014, pp. 026-032, vol. 1, No. 1, www.premierpublishers.org.
Jeffrey F. Kramer, et al. A New High Performance Quaternary Phosphonium Biocide for Microbiological Control in Oilfield Water Systems, Paper No. 08660, NACE International Corrosion 2008 Conference & Expo, 2008.
Chemical Reactivity of ClO2, Scotmas Group, http://www.scotmas.com/chlorine-dioxide/chemical-reactivity-of-clo2.aspx?locale=en, Apr. 24, 2018.
Water Technology & Chemicals, Red-Oxy, Method of Treating Oilfield Water, www.watchwater.de.
Gerard Muyzer. The ecology and biotechnology of sulphate-reducing bacteria, Nature Reviews, Microbiology, vol. 6, Jun. 2008, pp. 441-454, www.nature.com/reviews/micro.
Akyon, Benay. Biological Treatment of Hydraulic Fracturing Produced Water, Dissertation, Mar. 23, 2017.
Kim et al. "Isolation and Culture Conditions of a Klebsiella pneumoniae Strain That Can Utilize Ammonium and Nitrate Ions Simultaneously with Controlled Iron and Molybdate Ion Concentrations", Biosci. Biotechnol. Biochem., 66 (5), 996-1001, 2002.
Augustinovic et al., "Microbes—Oilfield Enemies or Allies?" Oilfield Review, Summer 2012:24, No. 2, pp. 4-17, 2012.
Braunstein et al., "Indole-positive Strains of Klebsiella pneumoniae Producing Hydrogen Sulfide in Iron—Agar Slants", downloaded from https://academic.oup.com/ajcp/article-abstract/65/5/702/1765452, Dec. 19, 2017.
Abdou, "Finding Value in Formation Water", Oilfield Review Spring 2011:23, No. 1, pp. 24-35, 2011.
Grab et al., "The Effect of Process Leak Contaminants on Biocidal Efficacy", 1994 Cooling Tower Institute Annual Meeting, Houston, TX, 8 pages, Feb. 1994.
Mccoy, "Microbiology of Cooling Water", Chemical Publishing Co., Inc., pp. 76-77, 1980.

* cited by examiner

WATER TREATMENT

FIELD OF THE INVENTION

The present invention relates to water treatment, particularly though not exclusively, to methods of treating aqueous systems to inhibit growth of micro-organisms.

BACKGROUND TO THE INVENTION

The presence and growth of micro-organisms in aqueous systems, especially in industrial water systems, is a concern. Examples of industrial water systems where micro-organisms are a concern include cooling water systems, pulping and papermaking systems and oil and gas field water systems.

The presence of micro-organisms in industrial water systems may result in the formation of deposits on system surfaces. These deposits or slime can give rise to various problems. In cooling water systems, slime may restrict water flow, reduce heat transfer efficiency, cause corrosion and may be aesthetically unappealing especially if algae are present due to their visible green pigmentation. Corrosion can also occur in industrial water systems in the absence of visible slime through the action of micro-organisms.

In pulp and paper mill systems, slime formed by micro-organisms may cause fouling, plugging, or corrosion of the system. The slime may also break loose and become entrained in the paper produced causing blemishes, holes, tears, and odour in the finished product. The end result may therefore be unusable product and wasted output.

Slime can also be a problem in oil and gas field water systems and may cause energy losses due to increased fluid frictional resistance, formation plugging and corrosion. The slime may harbour a mixture of aerobic and anaerobic bacteria that are responsible for the production of hydrogen sulfide gas. The hydrogen sulfide may cause souring of oil and gas which may reduce the quality of these products and increase treatment costs.

*Pseudomonas aeruginosa* bacteria are commonly present in air, water and soil. These bacteria continually contaminate open cooling water systems, pulping and papermaking systems and oil and gas field water systems and are among the most common slime formers. Slime may be viewed as being a mass of cells stuck together by the cementing action of the gelatinous secretions around each cell. The slime entraps other debris, restricts water flow and heat transfer and may serve as a site for corrosion.

*Chlorella vulgaris* algae are also commonly present in air, water and soil. These algae continually contaminate open cooling water systems and their growth turns the water and surfaces in these systems green. They also provide a food source for bacteria, which can stimulate slime formation, and protozoa which can harbour the pathogenic bacterium *Legionella pneumophila*.

A known method of controlling microbial growth in aqueous systems is to use biocides. While biocides are known to inhibit microbial growth the biocidal effect is generally of limited duration. The effectiveness of known biocides may be rapidly reduced as a result of exposure to negative influences. Negative influences may include temperature, pH or reaction with ingredients present in the system which neutralizes their biocidal effect. Therefore, the use of such biocides may involve continuous or frequent addition and their application at multiple sites or zones in the system to be treated. The cost of the biocide treatment and the labour costs associated with the application of known biocides may therefore be significant.

Known biocides are also highly toxic in the quantities known to be required for effective control of microbial populations. As a result, the amount of biocides that can be safely discharged into the environment may be limited by environmental regulations. Therefore, the need exists for improved methods for controlling microbial growth in aqueous systems.

As noted above, known biocides have a number of limitations including the large quantities of biocides which typically have to be used to achieve the desired biocidal effect and the potential harmful effects on the environment of biocides and therefore reducing the amount necessary for control and thus the quantity released to the environment has many benefits.

Accordingly, the present invention aims to address at least one disadvantage associated with the prior art whether discussed herein or otherwise.

SUMMARY OF THE INVENTION

According to the present invention there is provided a method of treating an aqueous system as set forth in the appended claims. Other features of the invention will be apparent from the claims, and the description which follows.

According to a first aspect of the present invention there is provided a method of treating an aqueous system to inhibit growth of one or more micro-organisms therein and/or to reduce the number of live micro-organisms therein, wherein the method comprises adding treatment agents to said aqueous system and wherein said treatment agents comprise:

(a) a phosphonium compound; and
(b) a halogen oxide compound.

The halogen oxide compound may comprise a chlorine compound. The halogen oxide compound may comprise a dioxide. The halogen oxide compound may comprise a chlorine oxide. The halogen oxide compound may comprise chlorine dioxide.

Suitably, the method comprises adding a phosphonium compound as a phosphonium compound composition. The method may comprise adding a phosphonium composition comprising one or more phosphonium compounds and water. The method may comprise adding a phosphonium composition comprising a single phosphonium compound and water.

Suitably, the method comprises adding a halogen oxide compound as a halogen oxide composition. The method may comprise adding a halogen oxide composition comprising one or more halogen oxides and water. The method may comprise adding a halogen oxide composition comprising a single halogen oxide and water.

The halogen oxide composition may comprise a halogen oxide and water. The halogen oxide composition may consist of a halogen oxide and water. The halogen oxide composition may comprise a chlorine compound and water. The halogen oxide composition may consist of a chlorine compound and water. The halogen oxide composition may comprise a chlorine oxide and water. The halogen oxide composition may consist of a chlorine oxide and water. The halogen oxide composition may comprise a dioxide and water. The halogen oxide composition may consist of a dioxide and water. The halogen oxide composition may comprise chlorine dioxide and water. The halogen oxide composition may consist of chlorine dioxide and water. The halogen oxide composition may comprise chlorine dioxide as the sole halogen oxide.

Suitably, the method comprises adding a halogen oxide composition which has an activity of at least 0.01% as halogen, for example at least: 0.1%; 0.2%; 0.3%; 0.4% or 0.5%. Suitably, the method comprises adding a halogen oxide composition which has an activity of at least 1% as halogen, for example at least: 2%; 3%; 4%; 5%; 6%; 7%; 8%; 9% or 10%. The halogen oxide (b) may have an activity of less than 20% as halogen, for example less than: 15%; 14%; 13%; 12%; 115 or 10%. The method may comprise adding a halogen oxide composition which has an activity of from 0.1% to 10.0% as halogen.

Suitably, the method comprises treating an aqueous system such that chlorine dioxide comprises greater than 50% of the total halogen oxide compound(s) added to the aqueous system. Suitably, the method comprises treating an aqueous system such that chlorine dioxide comprises greater than 90% of the total halogen oxide compound(s) added to the aqueous system, for example 99% or greater.

Suitably, the method comprises treating an aqueous system such that chlorine dioxide comprises greater than 50% of the total halogen oxide compound(s) present in the aqueous system. Suitably, the method comprises treating an aqueous system such that chlorine dioxide comprises greater than 90% of the total halogen oxide compound(s) present in the aqueous system, for example 99% or greater.

Suitably, the method employs chlorine dioxide as the only halogen oxide compound (b).

Suitably, there is provided a method of treating an aqueous system to inhibit growth of one or more micro-organisms therein and/or to reduce the number of live micro-organisms therein, wherein the method comprises adding treatment agents to said aqueous system and wherein said treatment agents comprise:
(a) a phosphonium compound; and
(b) chlorine dioxide.

Suitably, the method comprises treating an aqueous system to inhibit growth of anaerobic bacteria and/or to reduce the number of live anaerobic bacteria therein. Suitably, the method comprises treating an aqueous system to inhibit growth of facultative anaerobic bacteria and/or to reduce the number of live facultative anaerobic bacteria therein. Suitably, the method comprises treating an aqueous system to inhibit growth of aerobic bacteria and/or to reduce the number of live aerobic bacteria therein.

Suitably the aqueous system comprises a mixture of water and other constituents. The aqueous system may contain oil. The aqueous system may comprise an oil and water emulsion. The aqueous system may comprise solids. The aqueous system may comprise suspended solids. The aqueous system may comprise high levels of dissolved solids. The aqueous system may comprise one or more salts, for example sodium chloride.

Suitably, the method comprises treating an aqueous system which comprises dissolved solids.

Suitably, the method comprises treating an aqueous system having a total dissolved solids (TDS) of 1000 mg $l^{-1}$ or greater. Suitably, the aqueous system has a total dissolved solids (TDS) of at least 2000 mg $l^{-1}$, for example at least: 3000 mg $l^{-1}$; 4000 mg $l^{-1}$; 5000 mg $l^{-1}$; 6000 mg $l^{-1}$; 7000 mg $l^{-1}$; 8000 mg $l^{-1}$; or 9000 mg $l^{-1}$.

Suitably, the method comprises treating an aqueous system having a total dissolved solids (TDS) of 10,000 mg $l^{-1}$ or greater. Suitably, the aqueous system has a total dissolved solids (TDS) of at least 11,000 mg $l^{-1}$, for example at least: 12,000 mg $l^{-1}$; 13,000 mg $l^{-1}$; 14,000 mg $l^{-1}$; 15,000 mg $l^{-1}$; 16,000 mg $l^{-1}$; 17,000 mg $l^{-1}$; 18,000 mg $l^{-1}$; or 19,000 mg $l^{-1}$.

Suitably, the method comprises treating an aqueous system having a total dissolved solids (TDS) of 20,000 mg $l^{-1}$ or greater. Suitably, the aqueous system has a total dissolved solids (TDS) of at least 21,000 mg $l^{-1}$, for example at least: 22,000 mg $l^{-1}$; 23,000 mg $l^{-1}$; 24,000 mg $l^{-1}$; 25,000 mg $l^{-1}$; 26,000 mg $l^{-1}$; 27,000 mg $l^{-1}$; 28,000 mg $l^{-1}$; or 29,000 mg $l^{-1}$.

Suitably, the method comprises treating an aqueous system having a total dissolved solids (TDS) of 30,000 mg $l^{-1}$ or greater. Suitably, the aqueous system has a total dissolved solids (TDS) of at least 31,000 mg $l^{-1}$, for example at least: 32,000 mg $l^{-1}$; for example at least: 33,000 mg $l^{-1}$; 34,000 mg $l^{-1}$; 35,000 mg $l^{-1}$; 36,000 mg $l^{-1}$; 37,000 mg $l^{-1}$; 38,000 mg $l^{-1}$; 39,000 mg $l^{-1}$; or 40,000 mg $l^{-1}$.

The method may comprise treating an aqueous system having a total dissolved solids (TDS) of 50,000 mg $l^{-1}$ or greater. The aqueous system may have a total dissolved solids (TDS) of at least 60,000 mg $l^{-1}$, for example at least: 70,000 mg $l^{-1}$; 80,000 mg $l^{-1}$; 90,000 mg $l^{-1}$; 100,000 mg $l^{-1}$; 110,000 mg $l^{-1}$; 120,000 mg $l^{-1}$; 130,000 mg $l^{-1}$; 140,000 mg $l^{-1}$; 150,000 mg $l^{-1}$; 160,000 mg $l^{-1}$; 170,000 mg $l^{-1}$; 180,000 mg $l^{-1}$; 190,000 mg $l^{-1}$; 200,000 mg $l^{-1}$; 210,000 mg $l^{-1}$; 220,000 mg $l^{-1}$; 230,000 mg $l^{-1}$; 240,000 mg $l^{-1}$; or 250,000 mg $l^{-1}$; 260,000 mg $l^{-1}$; 270,000 mg $l^{-1}$; 280,000 mg $l^{-1}$; 290,000 mg $l^{-1}$; 300,000 mg $l^{-1}$.

Suitably, the method comprises treating an aqueous system having a total dissolved solids (TDS) of 250,000 mg $l^{-1}$ or less. The aqueous system may have a total dissolved solids (TDS) of no more than 240,000 mg $l^{-1}$, for example no more than 230,000 mg $l^{-1}$; 220,000 mg $l^{-1}$; 210,000 mg $l^{-1}$; 200,000 mg $l^{-1}$; 190,000 mg $l^{-1}$; 180,000 mg $l^{-1}$; 170,000 mg $l^{-1}$; 160,000 mg $l^{-1}$; 150,000 mg $l^{-1}$; 140,000 mg $l^{-1}$; 130,000 mg $l^{-1}$; 120,000 mg $l^{-1}$; or 110,000 mg $l^{-1}$.

Suitably, the method comprises treating an aqueous system having a total dissolved solids (TDS) of 100,000 mg $l^{-1}$ or less. The aqueous system may have a total dissolved solids (TDS) of no more than 90,000 mg $l^{-1}$, for example no more than 80,000 mg $l^{-1}$; 70.000 mg $l^{-1}$; 60,000 mg $l^{-1}$; 50,000 mg $l^{-1}$; or 40,000 mg $l^{-1}$.

Suitably, the method comprises treating an aqueous system having a total dissolved solids (TDS) of at least 25,000 mg $l^{-1}$. Suitably, the method comprises treating an aqueous system having a total dissolved solids (TDS) of at least 30,000 mg $l^{-1}$.

Suitably, the method comprises treating an aqueous system having a total dissolved solids (TDS) of from 10,000 mg $l^{-1}$ to 300,000 mg $l^{-1}$. Suitably, the method comprises treating an aqueous system having a total dissolved solids (TDS) of from 10,000 mg $l^{-1}$ to 100,000 mg $l^{-1}$. Suitably, the aqueous system has a total dissolved solids (TDS) of from 20,000 mg $l^{-1}$ to 100,000 mg $l^{-1}$, for example from 25,000 mg $l^{-1}$ to 100,000 mg $l^{-1}$. Suitably, the aqueous system has a total dissolved solids (TDS) of from 30,000 mg $l^{-1}$ to 100,000 mg $l^{-1}$. Suitably, the method comprises treating an aqueous system having a total dissolved solids (TDS) of from 20,000 mg $l^{-1}$ to 80,000 mg $l^{-1}$, for example from 25,000 mg $l^{-1}$ to 80,000 mg $l^{-1}$. Suitably, the method comprises treating an aqueous system having a total dissolved solids (TDS) of from 30,000 mg $l^{-1}$ to 80,000 mg $l^{-1}$.

Suitably, the method comprises treating an aqueous system to inhibit the growth of a plurality of different micro-organisms.

Suitably, the method comprises treating an aqueous system to prevent the growth of one or more micro-organisms. Suitably, the method comprises treating an aqueous system to prevent the growth of a plurality of different micro-organisms.

Suitably, the method comprises treating an aqueous system to kill one or more micro-organisms. Suitably, the method comprises treating an aqueous system to kill a plurality of different micro-organisms.

Suitably, the method comprises treating an aqueous system to inhibit or prevent the growth of one or more micro-organisms therein and/or to reduce the number of live micro-organisms therein, wherein said micro-organisms are selected from bacteria, fungi and algae. Suitably, the method comprises a method of inhibiting growth of bacteria and/or killing bacteria. Suitably, the method comprises a method of inhibiting growth of fungi and/or killing fungi. Suitably, the method comprises a method of inhibiting growth of algae and/or killing algae.

Suitably, the method comprises treating an aqueous system to inhibit or prevent the growth of anaerobic micro-organisms. Suitably, the method comprises treating an aqueous system to kill anaerobic micro-organisms. Suitably, the method comprises treating an aqueous system to inhibit or prevent the growth of anaerobic bacteria. Suitably, the method comprises treating an aqueous system to kill anaerobic bacteria. Suitably, the method comprises treating an aqueous system to inhibit or prevent the growth of facultative anaerobic bacteria. Suitably, the method comprises treating an aqueous system to kill facultative anaerobic bacteria.

Suitably, the method comprises treating an aqueous system to inhibit or prevent the growth of aerobic micro-organisms. Suitably, the method comprises treating an aqueous system to kill aerobic micro-organisms. Suitably, the method comprises treating an aqueous system to inhibit or prevent the growth of aerobic bacteria. Suitably, the method comprises treating an aqueous system to kill aerobic bacteria.

Suitably, the method comprises treating an aqueous system to inhibit or prevent the growth of anaerobic and aerobic micro-organisms. Suitably, the method comprises treating an aqueous system to kill anaerobic and aerobic micro-organisms. Suitably, the method comprises treating an aqueous system to inhibit or prevent the growth of anaerobic and aerobic bacteria. Suitably, the method comprises treating an aqueous system to kill anaerobic and aerobic bacteria.

The method may comprise a method of inhibiting growth of gram-positive aerobic bacteria, gram-positive facultative anaerobic bacteria, gram-negative aerobic bacteria, gram-negative facultative anaerobic bacteria, gram-positive anaerobic bacteria and/or gram-negative anaerobic bacteria. The method may comprise a method of inhibiting growth of mold and/or yeast. The method may comprise a method of inhibiting the growth of blue green algae and/or green algae. Suitably, the method comprises a method of inhibiting the growth of gram-negative aerobic bacteria, gram-negative facultative anaerobic bacteria, gram-negative anaerobic bacteria, and green algae. Suitably, the method comprises inhibiting the growth of *Pseudomonas aeruginosa* bacteria in an aqueous system. Suitably, the method comprises inhibiting the growth of *Enterobacter aerogenes* bacteria in an aqueous system. Suitably, the method comprises inhibiting the growth of *Desulfovibrio vulgaris* bacteria in an aqueous system. Suitably, the method comprises inhibiting the growth of *Chlorella vulgaris* algae in an aqueous system.

Suitably, the method comprises adding a phosphonium compound treatment agent and a halogen oxide compound treatment agent to an aqueous system such that a Log 10 reduction of 1 or greater in an anaerobe culture is obtained after a contact time of 1 hour. Suitably, the method comprises obtaining a Log 10 reduction of 2 or greater to an anaerobe culture after a contact time of 1 hour; for example of 3 or greater; 4 or greater; 5 or greater; or 6 or greater.

Suitably, the method comprises adding a phosphonium compound, and a halogen oxide compound to an aqueous system such that a complete kill of an anaerobe culture is obtained after a contact time of 1 hour.

Suitably, the method comprises obtaining a Log 10 reduction of 1 or greater to an anaerobe culture after a contact time of 10 minutes. Suitably, the method comprises obtaining a Log 10 reduction of 2 or greater to an anaerobe culture after a contact time of 10 minutes; for example of 3 or greater; 4 or greater; 5 or greater; or 6 or greater.

Suitably, the method comprises adding a phosphonium compound and a halogen oxide compound to an aqueous system such that a complete kill of an anaerobe culture is obtained after a contact time of 10 minutes.

Suitably, the method comprises adding a phosphonium compound treatment agent and a halogen oxide compound treatment agent to an aqueous system such that a Log 10 reduction of 1 or greater in a facultative anaerobe culture is obtained after a contact time of 1 hour. Suitably, the method comprises obtaining a Log 10 reduction of 2 or greater to a facultative anaerobe culture after a contact time of 1 hour; for example of 3 or greater; 4 or greater; 5 or greater; or 6 or greater.

Suitably, the method comprises adding a phosphonium compound, and a halogen oxide compound to an aqueous system such that a complete kill of a facultative anaerobe culture is obtained after a contact time of 1 hour.

Suitably, the method comprises obtaining a Log 10 reduction of 1 or greater to a facultative anaerobe culture after a contact time of 10 minutes. Suitably, the method comprises obtaining a Log 10 reduction of 2 or greater to a facultative anaerobe culture after a contact time of 10 minutes; for example of 3 or greater; 4 or greater; 5 or greater; or 6 or greater.

Suitably, the method comprises adding a phosphonium compound and a halogen oxide compound to an aqueous system such that a complete kill of a facultative anaerobe culture is obtained after a contact time of 10 minutes.

Suitably, the method comprises adding a phosphonium compound treatment agent and a halogen oxide compound treatment agent to an aqueous system such that a Log 10 reduction of 1 or greater in an aerobe culture is obtained after a contact time of 1 hour. Suitably, the method comprises obtaining a Log 10 reduction of 2 or greater to an aerobe culture after a contact time of 1 hour; for example of 3 or greater; 4 or greater; 5 or greater; or 6 or greater.

Suitably, the method comprises adding a phosphonium compound, and a halogen oxide compound to an aqueous system such that a complete kill of an aerobe culture is obtained after a contact time of 1 hour.

Suitably, the method comprises obtaining a Log 10 reduction of 1 or greater to an anaerobe culture after a contact time of 10 minutes. Suitably, the method comprises obtaining a Log 10 reduction of 2 or greater to an aerobe culture after a contact time of 10 minutes; for example of 3 or greater; 4 or greater; 5 or greater; or 6 or greater.

Suitably, the method comprises adding a phosphonium compound and a halogen oxide compound to an aqueous system such that a complete kill of an aerobe culture is obtained after a contact time of 10 minutes.

Suitably, the method comprises adding treatment agents to an aqueous system such that compound (a) and compound (b) are added to the aqueous system in a total amount of from 0.1 to 1000 parts by weight active per one million parts by weight of said aqueous system (ppm), for example from 0.1 to 100 ppm.

As used herein, all references to ppm refer to parts per million by weight unless stated otherwise.

Suitably, the method comprises adding compound (a) and compound (b) to the aqueous system such that they are added in a total amount of from 0.5 to 100 ppm, for example from 1 to 50 ppm. Suitably, the method comprises adding compound (a) and compound (b) to the aqueous system such that they are added in a total amount of from 1 to 40 ppm. Suitably, the method comprises adding compound (a) and compound (b) to the aqueous system such that they are added in a total amount of from 1 to 30 ppm. Suitably, the method comprises adding compound (a) and compound (b) to the aqueous system such that they are added in a total amount of from 1 to 20 ppm, for example 1 to 10 ppm.

Suitably, the method comprises adding a halogen oxide compound treatment agent to an aqueous system in an amount of at least 0.001 parts per million (ppm).

Suitably, the method comprises adding a halogen oxide compound treatment agent to an aqueous system to provide a treated aqueous system comprising said halogen oxide compound in an amount of at least 0.1 parts per million (ppm).

The method may comprise adding an aqueous solution comprising halogen oxide to an aqueous system. The method may comprise adding an aqueous solution comprising a stabilised halogen oxide to an aqueous system.

The method may comprise adding CDG Solution 3000 available from CDG Environmental, LLC as the halogen oxide composition, suitably in an amount of at least 0.05 ppm.

The method may comprise adding a halogen oxide composition which is generated in the field to an aqueous system. The method may comprise adding generated chlorine dioxide to an aqueous system.

Suitably, the method comprises adding a halogen oxide generated by a 2 pump or a 3 pump process.

Suitably, the method comprises adding chlorine dioxide generated by the reaction of a chlorite, a hypochlorite and an acid. The method suitably comprises adding chlorine dioxide generated by the reaction of sodium chlorite, sodium hypochlorite and hydrochloric acid.

Suitably, the method comprises adding chlorine dioxide generated by the reaction of a chlorite, a hypochlorite and an acid. The method suitably comprises adding chlorine dioxide generated by the reaction of sodium chlorite, sodium hypochlorite and hydrochloric acid.

Suitably, the method comprises adding chlorine dioxide generated by the reaction of a chlorite and a hypochlorite. Suitably, the method comprises adding chlorine dioxide generated by the reaction of a chlorite and hydrochloric acid.

Suitably, the method comprises adding chlorine dioxide generated by the reaction of a chlorite and chlorine. Suitably, the method comprises adding chlorine dioxide generated by the reaction of sodium chlorite and chlorine gas.

Suitably, the method comprises adding a halogen oxide compound to an aqueous system such that it is added in an amount of at least 0.05 ppm. Suitably, the method comprises adding a halogen oxide compound to an aqueous system such that it is added in an amount of at least 0.10 ppm. Suitably, the method comprises adding a halogen oxide compound to an aqueous system such that it is added in an amount of at least 0.5 ppm, for example at least 1 ppm. The method may comprise adding a halogen oxide to an aqueous system such that it is added in an amount of at least 10 ppm, for example at least 20 ppm; 30 ppm; 40 ppm; or 50 ppm.

Suitably, the method comprises adding a halogen oxide compound to an aqueous system such that it is present in an active residual amount of at least at least 0.05 ppm. Suitably, the method comprises adding a halogen oxide compound to an aqueous system such that it is present in an active residual amount of at least 0.10 ppm. Suitably, the method comprises adding a halogen oxide compound to an aqueous system such that it is present in an active residual amount of at least 0.15 ppm, for example at least: 0.20 ppm; or 0.25 ppm. The method may comprise adding a halogen oxide to an aqueous system such that it is present in an active residual amount of at least 0.30 ppm, for example at least 0.40 ppm; or 0.50 ppm.

The method may comprise adding a halogen oxide compound to an aqueous system such that it is present in an active residual amount of at least 0.50 ppm, for example at least 0.60 ppm; 0.70 ppm; 0.80 ppm; or 0.90 ppm.

Suitably, the method comprises adding a halogen oxide compound to an aqueous system such that it is added in an amount of not more than 500 ppm. Suitably, the method comprises adding a halogen oxide compound to an aqueous system such that it is added in an amount of not more than 400 ppm; for example not more than 300 ppm; 200 ppm or 100 ppm.

Suitably, the method comprises adding a halogen oxide compound to an aqueous system such that it is present in an active residual amount of not more than 50 ppm. Suitably, the method comprises adding a halogen oxide compound to an aqueous system such that it is present in an active residual amount of not more than 20 ppm, for example not more than 10 ppm. Suitably, the method comprises adding a halogen oxide compound to an aqueous system such that it is present in an active residual amount of not more than 9 ppm, for example not more than: 8 ppm; 7 ppm; 6 ppm; 5 ppm; 4 ppm; 3 ppm; or 2 ppm. Suitably, the method comprises adding a halogen oxide compound to an aqueous system such that it is present in an active residual amount of not more than 1.5 ppm, for example not more than: 1.4 ppm; 1.3 ppm; 12 ppm; 1.1 ppm; or 1.0 ppm. The method may comprise adding a halogen oxide compound to an aqueous system such that it is present in an active residual amount of not more than 0.90 ppm, for example not more than: 0.80 ppm; 0.70 ppm; or 0.60 ppm.

Suitably, the method comprises adding a halogen oxide compound to an aqueous system to provide a treated aqueous system comprising said halogen oxide in an amount of 0.05 to 1.00 ppm, for example 0.10 to 0.70 ppm.

Suitably, the method comprises adding chlorine dioxide to an aqueous system in an amount of at least 0.05 ppm. Suitably, the method comprises adding chlorine dioxide to an aqueous system in an amount of at least 0.10 ppm. Suitably, the method comprises adding chlorine dioxide to an aqueous system in an amount of at least 0.5 ppm, for example at least: 1 ppm. The method may comprise adding chlorine dioxide to an aqueous system in an amount of at least 10 ppm, for example at least 20 ppm; 30 ppm; 40 ppm; or 50 ppm.

Suitably, the method comprises adding chlorine dioxide to an aqueous system in an amount of not more than 500 ppm. Suitably, the method comprises adding chlorine dioxide to an aqueous system in an amount of not more than 400 ppm, for example not more than 300 ppm; 200 ppm or 100 ppm.

Suitably, the method comprises adding chlorine dioxide to an aqueous system such that it is present in an active residual amount of at least at least 0.05 ppm. Suitably, the method comprises adding chlorine dioxide to an aqueous system such that it is present in an active residual amount of at least 0.10 ppm. Suitably, the method comprises adding a chlorine dioxide to an aqueous system such that it is present in an active residual amount of at least 0.15 ppm, for example at least: 0.20 ppm; or 0.25 ppm. The method may comprise adding chlorine dioxide to an aqueous system such that it is present in an active residual amount of at least 0.30 ppm, for example at least 0.40 ppm; or 0.50 ppm.

Suitably, the method comprises adding chlorine dioxide to an aqueous system such that it is present in an active residual amount of not more than 50 ppm. Suitably, the method comprises adding chlorine dioxide to an aqueous system such that it is present in an active residual amount of not more than 20 ppm, for example not more than 10 ppm. Suitably, the method comprises adding a chlorine dioxide to an aqueous system such that it is present in an active residual amount of not more than 9 ppm, for example not more than: 8 ppm; 7 ppm; 6 ppm; 5 ppm; 4 ppm; 3 ppm; or 2 ppm. Suitably, the method comprises adding chlorine dioxide to an aqueous system such that it is present in an active residual amount of not more than 1.5 ppm, for example not more than: 1.4 ppm; 1.3 ppm; 1.2 ppm; 1.1 ppm; or 1.0 ppm. The method may comprise adding chlorine dioxide compound to an aqueous system such that it is present in an active residual amount of not more than 0.90 ppm, for example not more than: 0.80 ppm; 0.70 ppm; or 0.60 ppm.

Suitably, the method comprises adding chlorine dioxide to an aqueous system to provide a treated aqueous system comprising chlorine dioxide in an amount of 0.05 to 1.00 ppm, for example 0.10 to 0.70 ppm.

Suitably, the method comprises adding a phosphonium compound treatment agent to an aqueous system in an amount of at least 0.1 parts per million (ppm).

Suitably, the method comprises adding a phosphonium compound treatment agent to an aqueous system to provide a treated aqueous system comprising said phosphonium compound in an amount of at least 0.1 parts per million (ppm).

Suitably, the method comprises adding a phosphonium compound to an aqueous system such that it is added in an amount of at least 0.2 ppm. Suitably, the method comprises adding a phosphonium compound to an aqueous system such that it is added in an amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding a phosphonium compound to an aqueous system such that it is added in an amount of at least 1 ppm; for example at least 1.5 ppm: 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a phosphonium compound to an aqueous system such that it is added in an amount of at least 6 ppm, for example at least: 7 ppm; 8 ppm; 9 ppm; 10 ppm; 11 ppm; 12 ppm.

Suitably, the method comprises adding a phosphonium compound to an aqueous system such that it is present in an active amount of at least 0.2 ppm. Suitably, the method comprises adding a phosphonium compound to an aqueous system such that it is present in an active amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding a phosphonium compound to an aqueous system such that it is present in an active amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a phosphonium compound to an aqueous system such that it is present in an active amount of at least 6 ppm, for example at least: 7 ppm; 8 ppm; 9 ppm; 10 ppm; 11 ppm; 12 ppm.

Suitably, the method comprises adding a phosphonium compound treatment agent to an aqueous system to provide a treated aqueous system comprising said phosphonium compound added in an amount of 1 to 20 ppm, for example 1 to 15 ppm. Suitably, the method comprises adding a phosphonium compound treatment agent to an aqueous system to provide a treated aqueous system comprising said phosphonium compound added in an amount of 1 to 10 ppm, for example 2 to 8 ppm.

Suitably, the method comprises adding a phosphonium compound treatment agent to an aqueous system in an amount of not more than 250 ppm, for example not more than 125 ppm.

The method may comprise adding a phosphonium compound treatment agent to an aqueous system in an amount of not more than 100 ppm, for example not more than 50 ppm. The method may comprise adding a phosphonium compound to an aqueous system such that it is added in an amount of not more than 40 ppm, for example not more than 35 ppm. The method may comprise adding a phosphonium compound to an aqueous system such that it is added in an amount of not more than 30 ppm, for example not more than; 25 ppm; 20 ppm; 15 ppm; 10 ppm or 5 ppm.

Suitably, the method comprises adding a phosphonium compound treatment agent to an aqueous system to provide a treated aqueous system comprising said phosphonium compound in an active amount of not more than 250 ppm, for example not more than 125 ppm.

The method may comprise adding a phosphonium compound treatment agent to an aqueous system to provide a treated aqueous system comprising said phosphonium compound in an active amount of not more than 100 ppm, for example not more than 50 ppm. The method may comprise adding a phosphonium compound to an aqueous system such that it is present in an active amount of not more than 40 ppm, for example not more than 35 ppm. The method may comprise adding a phosphonium compound to an aqueous system such that it is present in an amount of not more than 30 ppm, for example not more than; 25 ppm; 20 ppm; 15 ppm; 10 ppm; or 5 ppm.

Suitably, the method comprises adding a phosphonium compound (a) and a halogen oxide compound (b) to an aqueous system in a weight ratio, expressed as active compound, of phosphonium compound:halogen oxide compound of from 1.0:50 to 100.0:1.0, for example from 1.0:25.0 to 50.0 to 1.0.

As used herein, all ratios are weight ratios unless stated otherwise.

Suitably, the method comprises adding a phosphonium compound (a) and a halogen oxide compound (b) to an aqueous system in a weight ratio, expressed as active compound, of phosphonium compound:halogen oxide compound of from 1.0:50.0 to 1.0:1.0, for example from 1.0:25.0 to 1.0:2.0.

Suitably, the method comprises adding a phosphonium compound (a) and a halogen oxide compound (b) to an aqueous system in a weight ratio, expressed as active compound, of phosphonium compound:halogen oxide compound of from 1.0:1.0 to 100.0:1.0, for example from 5.0:1.0 to 50.0 to 1.0.

Suitably the method comprises adding a phosphonium compound (a) and a halogen oxide compound (b) to an aqueous system to provide a treated aqueous system comprising said phosphonium compound (a) and said halogen oxide compound (b) in a weight ratio, expressed as active compound, respectively, of phosphonium compound:halogen oxide compound of from 7.0:1.0 to 35.0:1.0, for example from 10.0:1.0 to 35.0:1.0.

The method may comprise adding a phosphonium compound (a) and a halogen oxide compound (b) to an aqueous system to provide a treated aqueous system comprising said phosphonium compound (a) and said halogen oxide compound (b) in a weight ratio, expressed as active compound, of phosphonium compound:halogen oxide containing compound of at least 1.0:10.0, for example at least 1.0:2.0.

Suitably the method comprises adding a phosphonium compound (a) and a halogen oxide compound (b) to an aqueous system to provide a treated aqueous system comprising said phosphonium compound (a) and said halogen oxide compound (b) in a weight ratio, expressed as active compound, of phosphonium compound:halogen oxide compound of at least 1.0:1.0, for example of at least: 5.0:1.0, for example of at least: 10.0:1.0.

Suitably the method comprises adding a phosphonium compound (a) and a halogen oxide compound (b) to an aqueous system to provide a treated aqueous system comprising said phosphonium compound (a) and said halogen oxide compound (b) in a weight ratio, expressed as active compound, of phosphonium compound:halogen oxide containing compound of no greater than 100.0:1.0, for example no greater than 50.0:1.0, for example no greater than 30.0:1.0, The method may comprise adding a phosphonium compound (a) and a halogen oxide compound (b) to an aqueous system to provide a treated aqueous system comprising said phosphonium compound (a) and said halogen oxide compound (b) in a weight ratio, expressed as active compound, of phosphonium compound:halogen oxide containing compound of no greater than 1.0 to 1.0, for example no greater than 1.0:2.0, for example no greater than 1.0:10.0.

The method may comprise adding a combination of phosphonium compounds (a) to an aqueous system. Suitably, the method comprises adding a single type of phosphonium compound (a) to an aqueous system.

Suitably, the method employs a phosphonium compound (a) having formula:

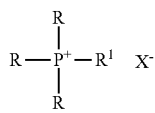

wherein each R is independently a $C_1$-$C_6$ alkyl group which is unsubstituted or substituted by a cyano, hydroxyl, esterified hydroxyl or aryl group:

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}C_{16}$ alkyl group. Suitably, $R^1$ is a tetradecyl group.

Suitably, X is chlorine.

Suitably, the method employs a phosphonium compound (a) which is a phosphonium chloride.

Suitably, the method comprises treating an aqueous system such that phosphonium chloride comprises greater than 50% of the total phosphonium compound(s) added to the aqueous system. Suitably, the method comprises treating an aqueous system such that phosphonium chloride comprises greater than 90% of the total phosphonium compound(s) added to the aqueous system, for example 99% or greater.

Suitably, the method comprises treating an aqueous system such that phosphonium chloride comprises greater than 50% of the total phosphonium compound(s) present in the aqueous system. Suitably, the method comprises treating an aqueous system such that phosphonium chloride comprises greater than 90% of the total phosphonium compound(s) present in the aqueous system, for example 99% or greater.

Suitably, the method employs a phosphonium chloride as the only phosphonium compound (a).

Suitably, the method comprises adding tri n-butyl n-tetradecyl phosphonium chloride (hereafter "TTPC") to the aqueous system. Suitably, the phosphonium compound (a) comprises TTPC. Suitably, the phosphonium compound (a) consists of TTPC.

Suitably, the method comprises adding an aqueous composition containing the phosphonium compound (a) to the aqueous system. Suitably, the method comprises adding an aqueous composition of TTPC to the aqueous system. The method may comprise adding an aqueous composition comprising 5% by weight of TTPC to the aqueous system. A suitable composition containing TTPC is available from BWA Water Additives and is sold under the trade name Bellacide 355 (an aqueous composition of TTPC and water consisting of water and 5% by weight of TTPC). The method may comprise adding an aqueous composition comprising 50% by weight of TTPC to the aqueous system. A suitable composition containing TTPC is available from BWA Water Additives and is sold under the trade name Bellacide 350 (an aqueous composition of TTPC and water consisting of water and 50% by weight of TTPC).

Suitably, the method comprises treating an aqueous system such that TTPC comprises greater than 50% of the total phosphonium compound(s) added to the aqueous system. Suitably, the method comprises treating an aqueous system such that TTPC comprises greater than 90% of the total phosphonium compound(s) added to the aqueous system, for example 99% or greater.

Suitably, the method comprises treating an aqueous system such that TTPC comprises greater than 50% of the total phosphonium compound(s) present in the aqueous system. Suitably, the method comprises treating an aqueous system such that TTPC comprises greater than 90% of the total phosphonium compound(s) present in the aqueous system, for example 99% or greater.

Suitably, the method employs TTPC as the only phosphonium compound (a).

The method may employ a synergistic mixture of compound (a) and compound (b). Suitably, by "synergistic mixture" it is meant that the mixture of compounds (a) and composition (b) has a synergistic effect on the inhibition of growth of one or more biological organisms, preferably micro-organisms such as bacteria, fungi and/or algae and/or has a synergistic effect on reducing the number of one or more biological organisms, preferably micro-organisms such as bacteria, fungi and/or algae.

The method may comprise adding compound (a) and compound (b) to the aqueous system such that the aqueous system comprises a synergistic mixture of compound (a) and compound (b).

The method may comprise adding compound (a) and compound (b) as a mixture to the aqueous system. The method may comprise adding compound (a) and compound (b) separately to the aqueous system and allowing or causing them to mix within the aqueous system.

Where the method comprises mixing compound (a) and compound (b) and adding the mixture to the aqueous system and/or adding compound (a) and compound (b) separately to the aqueous system and allowing or causing them to mix within the aqueous system then compound (a) and compound (b) are suitably used in the form of aqueous compositions.

Suitably, compound (a) is used in the form of an aqueous composition comprising between 1% and 90% by weight of compound (a), for example between 1% and 60% by weight. Suitably, compound (a) is used in the form of an aqueous composition comprising between 1% and 10% by weight of compound (a), for example 5% by weight.

Suitably, compound (b) is used in the form of an aqueous composition comprising between 0.01% and 20% by weight of compound (b), for example between 0.05% and 5.0%. Suitably, compound (b) is used in the form of an aqueous composition comprising between 0.1% and 3.0% by weight of compound (b), for example between 0.2% and 0.5%.

The method may comprise a method of treating an industrial water system. The method may comprise treating a cooling water system. The method may comprise treating a pulping and/or papermaking water system. The method may comprise treating an oil and/or gas field water system. The method may comprise treating an aqueous system to control the growth of bacterial and/or algal micro-organisms contained therein and/or which may become entrained in said system.

It has been found that the compositions and methods of utilisation of the present invention may in particular be efficacious in controlling acid producing facultative anaerobic bacteria and hydrogen sulphide producing anaerobic bacteria which may populate aqueous systems.

Surprisingly, it has been found that when compound (a) and compound (b) are combined the resulting combination may pose a higher degree of biocidal activity in an aqueous system than that of the individual compounds used alone. Because of the enhanced activity of the combination of treatment agent compounds, it may be possible for the total quantity of treatment agent added to an aqueous system to be reduced in comparison to a system using only one of said treatment agent compounds. In addition, the high degree of biocidal activity which is provided by each of the treatment agent compounds may be exploited without use of higher concentrations of each The combination of TTPC and chlorine dioxide may be particularly effective. The composition may also be surprisingly effective in systems having high total dissolved solids (TDS).

It has been found that the compositions and methods of utilisation of the present invention may in particular be efficacious in controlling the facultative anaerobic bacterium *Enterobacter aerogenes* and/or the anaerobic bacterium *Desulfovibrio vulgaris*, which may populate aqueous systems.

Surprisingly, the present inventor has found that mixtures of compound (a) and compound (b) such as mixtures of tri-n-butyl n-tetradecyl phosphonium chloride (TTPC) and chlorine dioxide are especially efficacious in controlling the growth of micro-organisms such as bacterial and algal microbes in aqueous systems comprising dissolved solids. The efficacy in relation to acid and sulphide producing bacteria is marked with certain selections of amounts and ratios of components and there is an unexpected synergistic relationship. It has been found that compositions of compounds (a) and compound (b) are unexpectedly effective against anaerobes such as *Desulfovibrio vulgaris*. It has been found that such compositions may have a marked synergy in relation to facultative anaerobes such as *Enterobacter aerogenes*.

It has been found that compositions are unexpectedly effective against facultative anaerobes and anaerobes. For example, chlorine dioxide may have some biocidal activity against facultative anaerobes and anaerobes at short contact times but the addition of TTPC may greatly improve performance even though TTPC alone may be ineffective against anaerobes or facultative aerobes at short contact times According to a second aspect of the present invention there is provided a method of treating an aqueous system to inhibit growth of one or more micro-organisms therein and/or to reduce the number of live micro-organisms therein, wherein the method comprises adding treatment agents to said aqueous system and wherein said treatment agents comprise:

(i) tri n-butyl n-tetradecyl phosphonium chloride (TTPC); and (ii) chlorine dioxide.

Suitably, the aqueous system comprises dissolved solids.

Suitably, the aqueous system comprises greater than 10,000 mg $l^{-1}$ total dissolved solids (TDS). The aqueous system may comprise greater than 20,000 mg $l^{-1}$ TDS, for example greater than 30,000 mg $l^{-1}$ TDS.

The method of the second aspect may comprise any feature as described in relation to the first aspect except where such features are mutually exclusive.

According to a third aspect of the present invention there is provided an aqueous system incorporating a combination of:

(a) a phosphonium compound; and (b) a halogen oxide compound.

Suitably, the aqueous system comprises dissolved solids.

Suitably, the aqueous system comprises greater than 10,000 mg $l^{-1}$ total dissolved solids (TDS). The aqueous system may comprise greater than 20,000 mg $l^{-1}$ TDS, for example greater than 30,000 mg $l^{-1}$ TDS.

Suitably, the phosphonium compound (a) has formula:

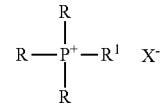

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, said compound (b) comprises chlorine dioxide.

The aqueous system of the third aspect may comprise any feature as described in relation to one or more of the first and/or second aspects except where such features are mutually exclusive.

According to a fourth aspect of the present invention there is provided a method of inhibiting or preventing the growth of one or more micro-organisms in an aqueous media, wherein the method comprises adding treatment agents to an aqueous media comprising dissolved solids and wherein said treatment agents comprise:

(a) a phosphonium compound; and
(b) a halogen oxide compound.

Suitably, the aqueous system comprises dissolved solids.

Suitably, the aqueous media comprises greater than 10,000 mg $l^{-1}$ total dissolved solids (TDS). The aqueous system may comprise greater than 20,000 mg $l^{-1}$ TDS, for example greater than 30,000 mg $l^{-1}$ TDS.

Suitably, the phosphonium compound (a) has formula:

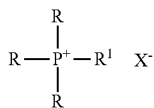

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, said compound (b) comprises chlorine dioxide.

The method of the fourth aspect may comprise any feature as described in relation to one or more of the first and/or second and/or third aspects except where such features are mutually exclusive.

According to a fifth aspect of the present invention there is provided an aqueous media comprising dissolved solids and incorporating a combination of:

(a) a phosphonium compound; and
(b) a halogen oxide compound.

Suitably, the aqueous media comprises greater than 10,000 mg $l^{-1}$ total dissolved solids (TDS). The aqueous system may comprise greater than 20,000 mg $l^{-1}$ TDS, for example greater than 30,000 mg $l^{-1}$ TDS.

Suitably, the phosphonium compound (a) has formula:

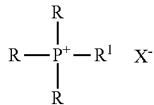

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, said compound (b) comprises chlorine dioxide.

The aqueous media of the fifth aspect may comprise any feature as described in relation to one or more of the first and/or second and/or third and/or fourth aspects except where such features are mutually exclusive.

According to a sixth aspect of the present invention there is provided a biocidal composition comprising a combination of:

(a) a phosphonium compound; and
(b) a halogen oxide compound.

Suitably, the phosphonium compound (a) has formula:

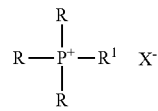

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, said compound (b) comprises chlorine dioxide.

The biocidal composition of the sixth aspect may comprise any feature as described in relation to one or more of the first and/or second and/or third and/or fourth and/or fifth aspects except where such features are mutually exclusive.

DETAILED DESCRIPTION OF PREFERRED EMBODIMENTS

The present invention will now be illustrated by way of example with reference to the following preferred embodiments.

EXAMPLES

Aqueous systems were treated by adding treatment agents comprising: (a) a phosphonium compound and (b) a halogen oxide compound. The phosphonium compound (a) used was TTPC. The halogen oxide compound (b) was chlorine dioxide.

A suspension of *Desulfovibrio vulgaris* plus *Enterobacter aerogenes* bacteria containing from $1\times10^5$ to $1\times10^6$ cells/mL was prepared in sterile pH 8 phosphate buffer containing sodium chloride to give the desired total dissolved solids (TDS) concentration. Aliquots of this suspension were dosed with the indicated concentrations of the compounds (a) and (b) with the concentrations being measured as ppm by weight of the stated composition in the dosed suspension.

The mixtures were allowed to stand at room temperature. At the designated contact times, each mixture was sampled to determine the total number of viable cells of both *Desulfovibrio vulgaris* and *Enterobacter aerogenes* by serial 10-fold dilution into API RP 38 media vials and anaerobic acid producing media vials, respectively. The vials were incubated at 37° C. for 72 hours. Results were recorded as $\log_{10}$ reduction in the viable count versus the control.

Aqueous media inoculated with anaerobe and aerobe culture and having a TDS of 30,000 mg $l^{-1}$ was treated with treatment agents comprising: (i) tri n-butyl n-tetradecyl phosphonium chloride (TTPC); (ii) chlorine dioxide; or (iii) a combination of TTPC and chlorine dioxide.

TTPC was used in the form of Bellacide 350, an aqueous composition of TTPC and water consisting of water and 50% by weight of TTPC available from BWA Water Additives.

Chlorine dioxide was used in the form of CDG Solution 3000 a 0.3% aqueous solution of chlorine dioxide available from CDG Environmental, LLC.

The efficacy of the treatment agents was evaluated by measuring the Log 10 Reduction of the anaerobic bacterium *Desulfovibrio vulgaris* and the facultative anaerobic bacterium *Enterobacter aerogenes* after contact times of 10 minutes, 30 minutes and 60 minutes as detailed in Table 1. For TTPC the stated ppm value relates to the amount of TTPC added (active). For the chlorine dioxide the stated ppm relates to the amount of free residual of chlorine dioxide.

TABLE 1

| Example | TDS (mg l$^{-1}$) | Contact time (minutes) | Treatment agent (ppm active) TTPC | Chlorine Dioxide | Log 10 Reduction Anaerobes* | Log 10 Reduction Facultative Anaerobes* |
|---|---|---|---|---|---|---|
| 1 | 30,000 | 10 | 3.125 | — | 0 | 0 |
| 2 | 30,000 | 10 | 6.25 | — | 0 | 0 |
| 3 | 30,000 | 10 | — | 0.25 | 3 | 3 |
| 4 | 30,000 | 10 | — | 0.5 | 4 | 6 |
| 5 | 30,000 | 10 | 3.125 | 0.25 | 5 | 6 |
| 6 | 30,000 | 10 | 6.25 | 0.25 | 5 | 6 |
| 7 | 30,000 | 30 | 3.125 | — | 0 | 0 |
| 8 | 30,000 | 30 | 6.25 | — | 2 | 1 |
| 9 | 30,000 | 30 | — | 0.25 | 3 | 3 |
| 10 | 30,000 | 30 | — | 0.5 | 5 | 6 |
| 11 | 30,000 | 30 | 3.125 | 0.25 | 5 | 6 |
| 12 | 30,000 | 30 | 6.25 | 0.25 | 5 | 6 |
| 13 | 30,000 | 60 | 3.125 | — | 0 | 0 |
| 14 | 30,000 | 60 | 6.25 | — | 5 | 1 |
| 15 | 30,000 | 60 | — | 0.25 | 3 | 3 |
| 16 | 30,000 | 60 | — | 0.5 | 5 | 6 |
| 17 | 30,000 | 60 | 3.125 | 0.25 | 5 | 6 |
| 18 | 30,000 | 60 | 6.25 | 0.25 | 5 | 6 |

*5 = complete kill for anaerobes
*6 = complete kill for facultative anaerobes

The results show that chlorine dioxide is effective against anaerobes and aerobes alone with short contact times but surprisingly, despite TTPC being ineffective alone at short contact times, the combination of TTPC and chlorine dioxide was markedly more effective against aerobes and anaerobes than chlorine dioxide alone.

Accordingly, it will be appreciated that combining TTPC and chlorine dioxide may allow for less chlorine dioxide to be used to achieve complete kill of aerobes and anaerobes compared to chlorine dioxide alone.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of treating an aqueous system to inhibit growth of *Desulfovibrio vulgaris* therein and/or to reduce the number of live *Desulfovibrio vulgaris* therein wherein the method comprises adding treatment agents to said aqueous system which has a total dissolved solids (TDS) of 10,000 mg $l^{-1}$ or greater and wherein said treatment agents comprise:

(a) a phosphonium compound consisting of tri n-butyl n-tetradecyl phosphonium chloride (TTPC); and (b) a halogen oxide compound consisting of chlorine dioxide;

wherein the treatment agents show greater performance of inhibiting growth or reducing the number of *Desulfovibrio vulgaris* than the sum of said treatment agents' individual performance; and wherein the method comprises adding said chlorine dioxide to said aqueous system such that it is present in an active residual amount of at least 0.05 parts per million (ppm); and wherein the method comprises adding the phosphonium compound (a) to said aqueous system in an amount of not more than 50 parts per million; and wherein the method comprises adding the phosphonium compound (a) and the halogen oxide compound (b) to an aqueous system in a weight ratio, expressed as active compound, of phosphonium compound:halogen oxide compound of from 1.0:25.0 to 50.0:1.0.

2. A method according to claim 1, wherein, the method comprises treating an aqueous system with a halogen oxide compound in addition to chlorine dioxide and wherein the content of chlorine dioxide is greater than 50% of the total halogen oxide compounds added to the aqueous system.

3. A method according to claim 1, wherein the method comprises treating an aqueous system having a total dissolved solids (TDS) of 30,000 mg l$^{-1}$ or greater.

4. A method according to claim 1, wherein the method comprises adding TTPC (a) to an aqueous system in an amount of at least 0.1 parts per million (ppm) and not more than 50 parts per million.

5. A method according to claim 1, wherein the aqueous system contains oil.

6. A method according to claim 1, wherein the aqueous system comprises sodium chloride.

7. A method according to claim 1, wherein the method comprises treating an oil and/or gas field water system.

8. A method of inhibiting the growth of *Desulfovibrio vulgaris* and *Enterobacter aerogenes* in an aqueous media, wherein the method comprises adding treatment agents to an aqueous media comprising dissolved solids such that it has a total dissolved solids (TDS) of 10,000 mg l$^{-1}$ to 30,000 mg l$^{-1}$ and wherein said treatment agents comprise:
(a) a phosphonium compound consisting of tri n-butyl n-tetradecyl phosphonium chloride (TTPC); and
(b) a halogen oxide compound consisting of chlorine dioxide;
wherein the treatment agents are added to the aqueous media in amounts configured to inhibit the growth of *Desulfovibrio vulgaris* and *Enterobacter aerogenes* in the aqueous media;
wherein the treatment agents show greater performance of inhibiting growth than the sum of said treatment agents' individual performance; and
wherein the method comprises adding said chlorine dioxide to said aqueous media such that it is present in an active residual amount of at least 0.05 parts per million (ppm); and
wherein the method comprises adding the phosphonium compound (a) to said aqueous media in an amount of not more than 50 ppm; and
wherein the method comprises adding the phosphonium compound and the halogen oxide compound to an aqueous media in a weight ratio, expressed as active compound, of phosphonium compound:halogen oxide compound of from 12.5:1.0 to 25:1.0.

9. A method of treating an aqueous system to inhibit growth of *Desulfovibrio vulgaris* and *Enterobacter aerogenes* micro-organisms therein and/or to reduce the number of live *Desulfovibrio vulgaris* and *Enterobacter aerogenes* micro-organisms therein, wherein the method comprises adding treatment agents to said aqueous system which has a total dissolved solids (TDS) of 10,000 mg l$^{-1}$ or greater and which contains oil and wherein said treatment agents comprise:
(i) a phosphonium compound consisting of tri n-butyl n-tetradecyl phosphonium chloride (TTPC); and
(ii) a halogen oxide compound consisting of chlorine dioxide;
wherein the treatment agents show greater performance of inhibiting growth or reducing the number of micro-organisms than the sum of said treatment agents' individual performance; and
wherein the method comprises adding said chlorine dioxide to said aqueous system such that it is present in an active residual amount of at least 0.05 parts per million (ppm); and
wherein the method comprises adding the phosphonium compound (a) to said aqueous system in an amount of not more than 50 ppm; and
wherein the method comprises adding the phosphonium compound and the halogen oxide compound to an aqueous system in a weight ratio, expressed as active compound, of phosphonium compound:halogen oxide compound of from 1.0:25.0 to 50.0:1.0.

10. A method according to claim 9, wherein the method comprises treating an aqueous system having a total dissolved solids (TDS) of 30,000 mg l$^{-1}$ or greater and wherein the method comprises adding TTPC to an aqueous system in an amount of at least 0.1 parts per million (ppm) and adding chlorine dioxide to an aqueous system such that it is present in an active residual amount of at least 1 parts per million (ppm).

11. A method according to claim 9, wherein the aqueous system contains oil and sodium chloride.

12. A method according to claim 9, wherein the method comprises adding TTPC and chlorine dioxide to an aqueous system in a weight ratio, expressed as active compound, of TTPC:chlorine dioxide of from 12.5:1 to 25:1.

13. A method according to claim 9, wherein the method comprises adding treatment agents to an aqueous system comprising dissolved solids such that it has a total dissolved solids (TDS) of 30,000 mg l$^{-1}$ or greater.

14. A method according to claim 9, wherein the method comprises adding treatment agents to an aqueous system comprising dissolved solids such that it has a total dissolved solids (TDS) of 30,000 mg l$^{-1}$ or greater and wherein the method comprises adding chlorine dioxide such that it is present in an active residual amount of not more than 1.5 ppm and adding a phosphonium compound such that it is present in an amount of not more than 10 ppm.

15. A method according to claim 9, wherein the method comprises adding treatment agents to an aqueous system comprising dissolved solids such that it has a total dissolved solids (TDS) of 30,000 mg l$^{-1}$ or greater and wherein the method comprises adding chlorine dioxide such that it is present in an active residual amount of not more than 5 ppm and adding a phosphonium compound such that it is present in an amount of not more than 15 ppm.

16. A method comprising:
adding treatment agents to an aqueous system, the aqueous system comprising dissolved solids such that it has a total dissolved solids (TDS) of 10,000 mg l$^{-1}$ to 250,000 mg l$^{-1}$, and containing *Desulfovibrio vulgaris* and *Enterobacter aerogenes*, the treatment agents comprising a combination of:
(a) a phosphonium compound consisting of tri n-butyl n-tetradecyl phosphonium chloride (TTPC); and (b) a halogen oxide compound consisting of chlorine dioxide;

wherein the combination of TTPC and halogen oxide compound are added to the aqueous system in amounts configured to reduce the number of live *Desulfovibrio vulgaris* and *Enterobacter aerogenes* in the aqueous system;

wherein the combination shows greater performance of reducing the number of live *Desulfovibrio vulgaris* and *Enterobacter aerogenes* than the sum of said treatment agents' individual performance;

wherein the method comprises adding said chlorine dioxide to said aqueous media such that it is present in an active residual amount of at least 0.05 parts per million (ppm);

wherein the method comprises adding the phosphonium compound (a) to said aqueous system in an amount of not more than 50 ppm; and wherein the method comprises adding the phosphonium compound and the halogen oxide compound to an aqueous system in a weight ratio, expressed as active compound, of phosphonium compound:halogen oxide compound of from 1.0:25.0 to 50.0:1.0.

17. A method according to claim 16, wherein the method comprises adding the phosphonium compound and the halogen oxide compound to an aqueous system in a weight ratio, expressed as active compound, of phosphonium compound: halogen oxide compound of from 5.0:1.0 to 50.0:1.0 and wherein the aqueous system has a total dissolved solids (TDS) of 10,000 mg $l^{-1}$ to 100,000 mg $l^{-1}$.

* * * * *